United States Patent [19]

Moyers

[11] Patent Number: 5,108,413
[45] Date of Patent: Apr. 28, 1992

[54] DILATOR FOR OPENING THE LUMEN OF A TUBULAR ORGAN

[76] Inventor: Robert E. Moyers, 1035 Country Club Dr., Ann Arbor, Mich. 48105

[21] Appl. No.: 630,874

[22] Filed: Dec. 20, 1990

[51] Int. Cl.⁵ ............................................ A61M 29/00
[52] U.S. Cl. .................................................... 606/191
[58] Field of Search ............ 606/191, 192, 193, 194, 606/195, 196, 197, 198; 604/104, 107

[56] References Cited

U.S. PATENT DOCUMENTS

| | | | |
|---|---|---|---|
| 4,160,448 | 7/1979 | Jackson | 128/673 |
| 4,405,320 | 9/1983 | Cracauek et al. | 604/175 |
| 4,417,888 | 11/1983 | Consentino et al. | 604/175 |
| 4,496,350 | 1/1985 | Consentino | 604/175 |
| 4,619,641 | 10/1986 | Schanzer | 604/86 |
| 4,654,033 | 3/1987 | Lapeyre et al. | 604/175 |
| 4,657,553 | 4/1987 | Taylor | 623/66 |
| 4,729,766 | 3/1988 | Bergentz et al. | 623/1 |
| 4,941,871 | 7/1990 | Ward | 600/36 |
| 5,019,096 | 5/1991 | Fox, Jr. et al. | 604/265 |

Primary Examiner—C. Fred Rosenbaum
Assistant Examiner—M. Mendez
Attorney, Agent, or Firm—Harness, Dickey & Pierce

[57] ABSTRACT

A dilator is disclosed for use in opening the lumen of a tubular organ utilizing a expansion member made of a material having a negative Poisson ratio such as polytetrafluorethylene. The negative Poisson ratio of the expansion member enables the member, when stretched, to expand radially outwardly rather than thinning in a radial direction to perform useful work in opening the lumen in a tubular organ such as in performing coronary angioplasty.

16 Claims, 2 Drawing Sheets

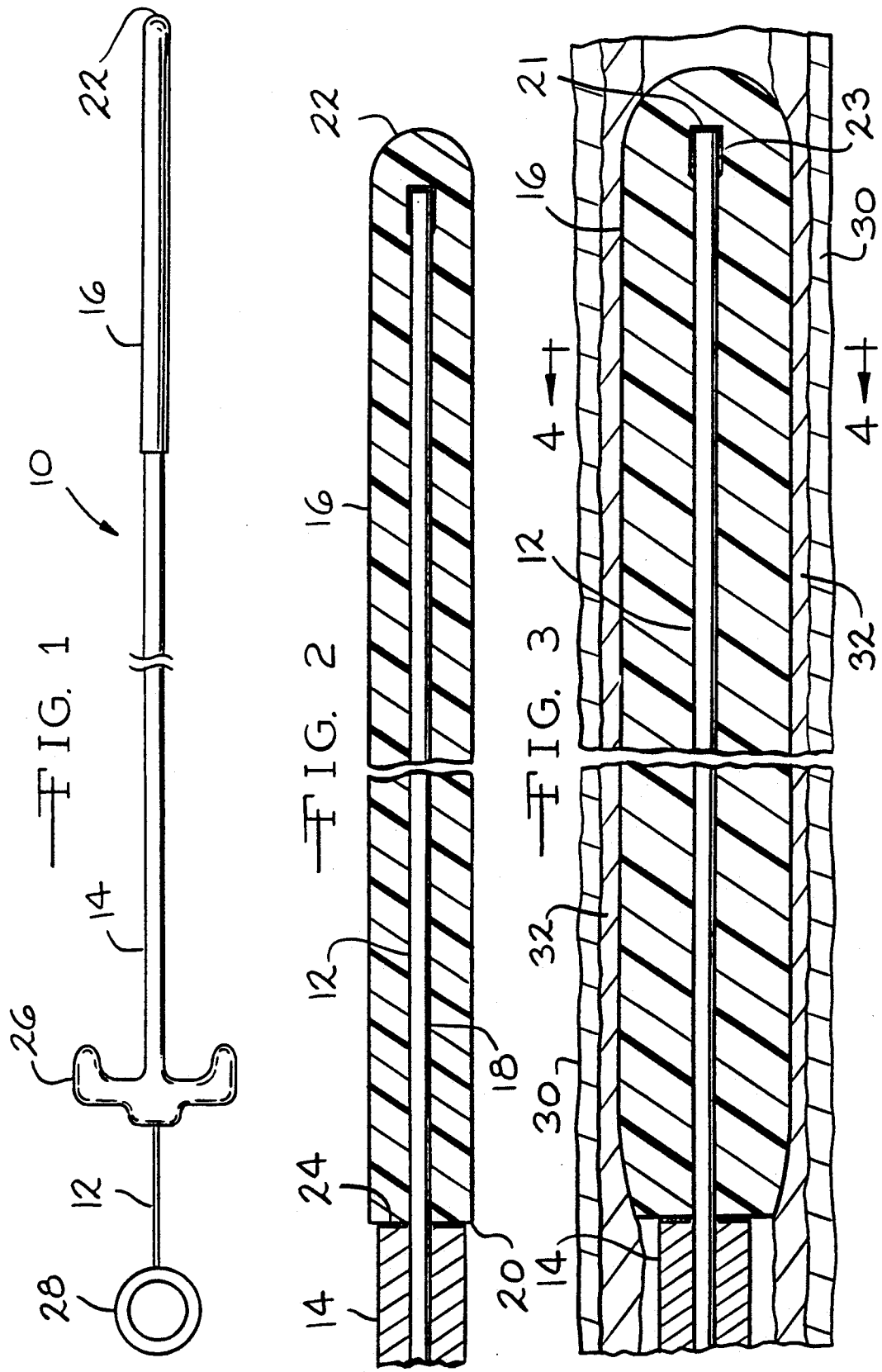

DILATOR FOR OPENING THE LUMEN OF A TUBULAR ORGAN

BACKGROUND AND SUMMARY OF INVENTION

This invention relates to a dilator for use in opening the lumen in tubular body organs such as in percutaneous transluminal coronary angioplasty (PTCA) and in particular to a dilator utilizing a material having a negative Poisson ratio which expands in thickness upon stretching to thereby open the lumen.

PTCA is the most frequently performed coronary revascularization procedure. Most PTCAs are balloon angioplasties, a procedure in which a balloon is inserted through the patient's vascular system to the site of an atheroma and inflated to compress, reshape and redistribute the accumulated material comprising the atheroma. A marked increase of blood flow through the artery is provided in most cases.

While balloon dilation catheters have been extremely successful in performing angioplasty, there are several disadvantages to a balloon catheter. The primary disadvantage or problem with the balloon catheter is its size. Use of balloon catheters is currently restricted to the larger coronary arteries. A device which can be used to perform PTCA in small coronary arteries would have a tremendous benefit in terms of improving the supply of blood to the heart. Other disadvantages of balloon catheters include problems with control of the inflation pressure, maintenance of the balloon position while the pressure is applied and complications arising from bursting of the balloon. The extent of balloon expansion as it is inflated is difficult to control and varies depending upon the resistance provided by the artery itself. It is easy to over inflate the balloon, applying excessive pressure directly on the atheromatous lesion and damaging the wall structure of the artery.

Accordingly, it is the object of the present invention to provide a dilator which overcomes the above disadvantages and problems associated with balloon dilation catheters.

It is a further object to provide a dilator in which the radial expansion of the dilator is both known and controllable.

The dilator of the present invention utilizes a hollow rod of expanded polytetrafluorethylene (PTFE) having a negative Poisson ratio. The Poisson ratio of a material relates stretching to thinning. Most materials tend to roughly maintain their volume when stretched or compressed. As a result, when stretched, most materials will thin and when compressed they become thicker. However, it has recently been discovered that expanded PTFE behaves in the opposite manner, i.e. it becomes thicker when stretched rather than thinner. Such a material is said to have a negative Poisson ratio.

The dilator includes a hollow rod or sheath of the PTFE near its distal end. When placed in the coronary artery at the desired location, it is pulled lengthwise, stretched, so as to expand radially outwardly, applying pressure to the atheroma in the artery and, as a result, compresses, reshapes and redistributes the accumulated material opening the lumen of the artery.

The use of a negative Poisson ratio material in a dilator avoids the need to inflate an expandable member such as a balloon to compress the atheroma. Without the need for inflation, there is no concern with control of inflation pressure or problems associated with a leak of the inflation medium. The amount of radial expansion of the PTFE can be easily controlled by the physician performing the procedure by controlling proximally the amount of stretching of the PTFE. Dilators can be made with various diameters to suit the needs of individual patients.

During an angioplasty procedure, several dilators can be used in a series with each successive dilator having a slightly larger diameter and slightly larger controlled distention.

While the invention is described in the context of a dilator for use in coronary angioplasty, it should be understood that the dilator can be used in any procedure which opens the lumen of a body structure by the application of pressure from within the lumen, e.g. including opening of occluded fallopian tubes or cystoscopic relief of closing of the urethra associated with prostatitis.

Further objects, features and advantages of the invention will become apparent from a consideration of the following description and the appended claims when taken in consideration with the accompanying drawings.

BRIEF DESCRIPTION OF THE DRAWINGS

FIG. 1 is an elevational view of the dilator of the present invention;

FIG. 2 is a cross sectional view of the distal end of the dilator shown in FIG. 1;

FIG. 3 is a cross sectional view of the distal end of the dilator placed in an artery and stretched longitudinally to expand radially;

DETAILED DESCRIPTION OF THE INVENTION

Figure 4:
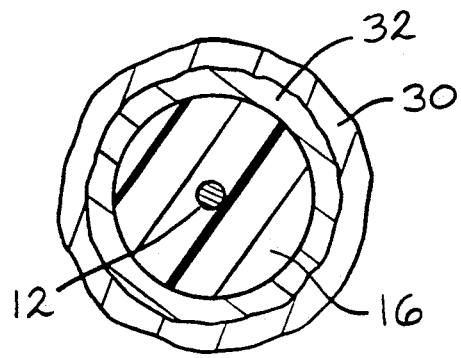
FIG. 4 is a cross sectional view of the dilator and artery as seen from the line 4—4 of FIG. 3.

The dilator of the present invention is shown in FIG. 1 and designated generally at 10. Dilator 10 is constructed of an inner guide wire 12 which extends through a elongated flexible outer tubular member or catheter 14. An elongated expansion member 16 of expanded PTFE is mounted to the distal end 24 of the tube member 14. The PTFE member 16 is tubular as shown in FIG. 2 having a central lumen 18. The expansion member 16 is opened at its proximal end 20 while the distal end 22 is closed. The central lumen 18 extends through the member 16 and terminates at end 21 adjacent the closed end 22 of the expansion member 16. The guide wire 12, which extends through the catheter 14, continues into the expansion member 16 and terminates at the end 21 of the lumen 18. The end of guide wire 12 is secure to the expansion member by any means, such as by adhesive 23.

At the proximal end of the dilator 10, the flexible catheter 14 includes a finger grip 26 for the forefinger and middlefinger of the operator while the proximal end of the guide wire 12, which extends beyond the finger grip 26, includes a thumb grip 28. The two grips 26 and 28 enable an user of the dilator to slide the guide wire 12 longitudinally within the flexible catheter 14 in the same manner as a hypodermic syringe is operated. Movement of the guide wire 12 in a direction toward the distal end of the catheter 10 results in longitudinal stretching of the tubular PTFE body 16.

Since the expansion member 16 has a negative Poisson ratio, when it is stretched, it expands radially rather than thins. The radial expansion of the member enables the PTFE to be used to perform lumen opening procedures such as angioplasty as shown in FIG. 3. There, the expansion member 16 has been positioned within artery 30 at the site where atheroma 32 has significantly reduced the lumen of the artery. Once positioned, the finger and thumb grips 26 and 28 are manipulated to push the thumb grip 28 toward the finger grip 26 causing the guide wire 12 to slide within catheter 14, longitudinally stretching the expansion member. The stretching causes the member to expand radially outwardly, compressing, reshaping and redistributing the accumulated plaque forming the atheroma.

The overall length of the dilator 10 is on the order of 4½ to 5 feet to enable the dilator to be inserted into a patient's vascular system through the skin in either the leg or arm and fed through the vascular system to the coronary artery in need of treatment. The insertion and routing of the dilator is accomplished by the well known procedures for performing percutaneous transluminal coronary angioplasty. The dilator is flexible enough to be routed through the vascular system yet stiff enough to enable the operator to control the path and operation of the dilator from its proximal end.

The size of the expansion member 16 as well as the guide wire 12 and catheter 14 can be varied depending upon the specific requirements. These components can be manufactured in a size small enough to be inserted in smaller coronary arteries than is possible with current balloon devices. Additionally, the length of the expansion member 16 can be varied as well as the stiffness of the guide wire 12 and catheter 14.

In operation, depending upon the nominal size of the artery and the extent of the blockage, a first relatively small dilator can be inserted into the artery and used to compress the deposits and increase the lumen of the artery. After removal, a dye can be inserted into the blood stream to visualize the extent to which the artery has been opened. If necessary, a larger size dilator is then inserted to further compress the accumulated deposits, further opening the artery. This process of opening the artery and subsequently visualizing the improved blood flow can be repeated as necessary to obtain the desired improvement in blood flow.

Figure 5:
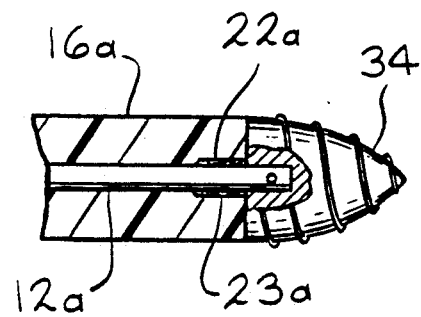
FIG. 5 is a partial sectional and partial elevational view of the distal end of an alternative embodiment of the dilator of the present invention.
Figure 6:
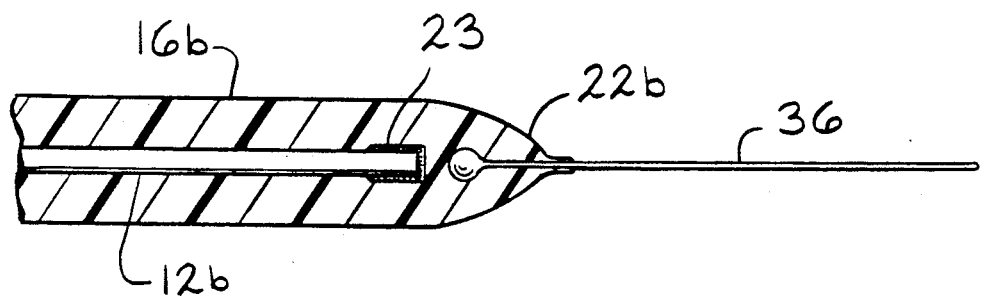
FIG. 6 is a partial sectional and partial elevational view of the distal end of another alternative embodiment.
Figure 7:
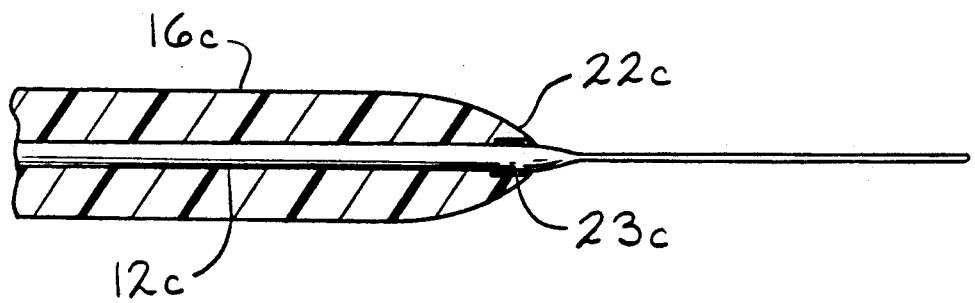
FIG. 7 is a partial sectional and partial elevational view of the distal end of yet another alternative embodiment.

Modified embodiments of the present invention are shown in FIGS. 5, 6 and 7. In FIG. 5, the distal end of the dilator is equipped with an auger tip 34 having an exterior spiral thread which is useful in routing the dilator through the deposits in the artery. The auger tip 34 is coupled to the distal end 22a of the expansion member 16a and also to the distal end of the guide wire 12a. Upon rotation of the dilator, the spiral thread of tip 34 draws the dilator through the artery.

In FIG. 6, a secondary guide wire 36 extends longitudinally from the distal end 22b of the expansion member 16. The secondary guide wire is also useful in routing the dilator through a clogged artery and is generally made of a wire that is more flexible than the guide wire 12b.

FIG. 7 discloses another embodiment which is similar to that shown in FIG. 6 only instead of using a second guide wire extending from the dilator, the guide wire 12c extends through the expansion member 16c beyond its distal end 22c providing a longitudinal extension for guiding the dilator through the patient's vascular system. The guide wire 12c is secured to the distal end 22c of the expansion member by adhesive 40 or other means so as to ensure that the longitudinal movement of guide wire 12c within the tube 14 results in stretching of the PTFE body. If desired, the extending portion of guide wire 12c can be made more flexible than the remaining portion of the guide wire to aid in routing the catheter through the vascular system. This can be accomplished in a well known manner such as by reducing the cross sectional area of the wire. The guide wire and tip can be made of any suitable metal for surgical procedures such as stainless or, most preferably, a nickel-titanium alloy.

The expansion member 16, having a known Poisson ratio, enables the operator to precisely control the extent of radial expansion of the member by controlling the extent by which it is stretched and by so doing, controlling the applied pressure. Expansion of the expansion member is a direct function of its Poisson ratio and does not depend upon the amount of resistance to expansion provided by the artery and the atheroma as in the case with an inflatable balloon. The amount of pressure achieved each time is known and controlled so damage to the artery wall is obviated. Furthermore, there is no concern with bursting of and leak of the dilator as with a balloon catheter.

While the invention has been shown and described in connection with percutaneous transluminal coronary angioplasty, the dilator of the present invention can be used in performing non-coronary angioplasty and also in non-angioplasty dilation procedures where balloon catheters are presently in use.

It is to be understood that the invention is not limited to the exact construction or method illustrated and described above, but that various changes and modifications may be made without departing from the spirit and scope of the invention as defined in the following claims.

I claim:

1. A dilator for opening the lumen of a tubular organ comprising:
    an elongated flexible expansion member of a material having a negative Poisson ratio;
    means for guiding said expansion member through the lumen to a desired location by manipulation of said guide means exteriorly of said lumen; and
    means for stretching said expansion member lengthwise whereby due to the negative Poisson ratio of said member, said member expands transversely of the length of said expansion member.

2. The dilator of claim 1 wherein said elongated flexible expansion member is expanded polytetrafluoroethylene.

3. The dilator of claim wherein said elongated flexible expansion member has a distal end and a proximal end; said guide means includes a catheter having a distal end and a proximal end with the distal end coupled to the proximal end of said expansion member and being of sufficient length that the proximal end of said catheter extends exteriorly of said lumen when said expansion member is positioned at the desired location in said lumen and a guide wire extending through said catheter having a distal end coupled to the distal end of said expansion member and having a proximal end extending from the proximal end of said catheter; and said stretching means including means coupled to the proximal ends of said catheter and said guide wire for moving said guide wire longitudinally through said catheter whereby said expansion member is stretched upon movement of said guide wire toward the distal end of said expansion member.

4. The dilator of claim 3 wherein said stretching means includes finger and thumb grip means coupled to the proximal ends of said catheter and guide wire.

5. The dilator of claim 3 further comprising a central passage in said expansion member extending from the proximal end thereof and terminating adjacent the distal end thereof with said guide wire extending through said central passage.

6. The dilator of claim 3 further comprising tip means at the distal end of said expansion member forming threads for moving said expansion member through said lumen upon rotation of said catheter, guide wire and expansion member.

7. The dilator of claim 3 further comprising an elongated pliant wire tip extending longitudinally from the distal end of said expansion member.

8. The dilator of claim 3 wherein said expansion member is a hollow rod of polytetrafluorethylene.

9. The dilator of claim 1 wherein said expansion member is a hollow rod of polytetrafluorethylene.

10. A dilator for performing angioplasty comprising:
an elongated flexible expansion member of a material having a negative Poisson ratio having proximal and distal ends;
a tubular elongated flexible outer member having proximal and distal ends with said distal end coupled to the proximal end of said expansion member; and
an elongated flexible inner member extending through said outer member and having proximal and distal ends with the distal end coupled to said expansion member near the distal end thereof and with the proximal end projecting from the proximal end of said outer member;
said outer and inner members being of sufficient length to extend through a patient's vascular system from an opening therein to a location in need of treatment to position said expansion member at said location;
means for moving said inner member longitudinally within said outer member in a direction toward the distal end thereof to stretch said expansion member longitudinally whereby said member expands transversely due to the negative Poisson ratio of said expansion member.

11. The dilator of claim 10 wherein said expansion member is a hollow tube of expanded polytetrafluorethylene.

12. The dilator of claim 11 wherein said inner member extends through said hollow tube to the distal end thereof where said inner member is coupled thereto.

13. The dilator of claim 10 further comprising tip means extending from the distal end of said expansion member for guiding said expansion member through the lumen of said patient's vascular system.

14. The dilator of claim 13 wherein said tip means includes a spiral grooved tip member.

15. The dilator of claim 13 wherein said tip means includes a pliant guide wire extending from said expansion member.

16. The dilator of claim 15 wherein said pliant guide wire is made of a nickel titanium alloy.

* * * * *